US008325049B2

(12) United States Patent
Deacon

(10) Patent No.: US 8,325,049 B2
(45) Date of Patent: Dec. 4, 2012

(54) METHOD AND SYSTEM FOR MEASURING TEMPERATURE AND PRESSURE IN DIFFERENT REGIONS TO DETERMINE STEAM QUALITY

(75) Inventor: Walter T. Deacon, West Lafayette, IN (US)

(73) Assignee: Thermo Diagnostics Company LLC, West Lafayette, IN (US)

( * ) Notice: Subject to any disclaimer, the term of this patent is extended or adjusted under 35 U.S.C. 154(b) by 780 days.

(21) Appl. No.: 12/498,160

(22) Filed: Jul. 6, 2009

(65) Prior Publication Data

US 2011/0000281 A1    Jan. 6, 2011

(51) Int. Cl.
    *G08B 21/00* (2006.01)
(52) U.S. Cl. .......................... 340/603; 340/540; 73/29.01
(58) Field of Classification Search .................. 340/540, 340/603; 73/29.01, 29.03
    See application file for complete search history.

(56) References Cited

U.S. PATENT DOCUMENTS

| | | | |
|---|---|---|---|
| 392,980 A | 11/1888 | Barrus | 374/42 |
| 401,111 A | 4/1889 | Barrus | 374/42 |
| 465,321 A | 12/1891 | Gehre | 374/42 |
| 494,710 A | 2/1893 | Carpenter | 374/42 |
| 494,057 A | 3/1893 | Carpenter | 374/42 |
| 550,814 A | 12/1895 | Barrus | 374/42 |
| 575,391 A | 1/1897 | Carpenter | 374/42 |
| 857,984 A | 6/1907 | Ellison | 374/42 |
| 1,042,782 A | 10/1912 | Cardner | 374/42 |
| 1,043,983 A | 11/1912 | Thomas | 73/204.27 |
| 1,087,929 A | 2/1914 | Dodge | 73/861.49 |
| 1,093,244 A | 4/1914 | Berry | 346/4 |
| 1,108,278 A | 8/1914 | Thomas | 73/863.82 |
| 1,127,692 A | 2/1915 | Spitzglass | 73/861.65 |
| 1,156,503 A | 10/1915 | Sheldon | 73/204.13 |
| 1,185,734 A | 6/1916 | Trood | 73/861.81 |
| 1,193,488 A | 8/1916 | Thomas | 73/202 |
| 1,214,853 A | 2/1917 | Weil | 73/861.52 |
| 1,279,485 A | 9/1918 | Winslow | 73/295 |
| 1,314,249 A | 8/1919 | Crowell | 73/204.11 |
| 1,430,731 A | 10/1922 | Goodell | 73/203 |
| 1,666,628 A | 4/1928 | Franz | 73/112.02 |
| 1,679,293 A | 7/1928 | Dawley | 73/861.02 |
| 1,697,344 A | 1/1929 | Grant | 73/861.61 |
| 1,726,463 A | 8/1929 | Guido | 73/203 |
| 1,742,203 A | 1/1930 | Ellison | 374/42 |
| 1,789,705 A | 1/1931 | Hamilton | 374/42 |
| 1,858,409 A | 5/1932 | Erich | 73/73 |
| 1,953,061 A | 4/1934 | Blackwood | 48/83 |
| 2,120,874 A | 6/1938 | Stone | 374/42 |
| 2,146,312 A | 2/1939 | Powell | 324/443 |
| 2,252,367 A | 8/1941 | Germer | 73/196 |
| 2,387,717 A | 10/1945 | Alick | 236/32 |
| 3,100,395 A | 8/1963 | Morley | 374/42 |
| 3,181,363 A | 5/1965 | Edmonson | 374/134 |
| 3,322,934 A | 5/1967 | Albert | 219/523 |
| 3,324,710 A | 6/1967 | Calkins | 73/29.01 |
| 3,363,460 A | 1/1968 | Baumann | 374/42 |
| 3,370,155 A | 2/1968 | Belliveau | 219/406 |
| 3,521,479 A | 7/1970 | Carter | 73/28.01 |
| 3,596,516 A | 8/1971 | Haynes, Jr. | 374/42 |
| 4,034,597 A | 7/1977 | Fredriksson | 73/29.03 |

(Continued)

*Primary Examiner* — Jeffery Hofsass
(74) *Attorney, Agent, or Firm* — Dowell IP, P.C.

(57) ABSTRACT

A method and apparatus for monitoring the quality of steam used in a process is disclosed. A pressure and temperature sensor is exposed to the steam on either side of an inline pressure drop device such as an orifice or pressure reducing valve. The measurements are transmitted to a controller that calculates the steam quality percentage or superheat value. An alarm is issued if the steam quality is beyond a predetermined tolerance.

21 Claims, 5 Drawing Sheets

U.S. PATENT DOCUMENTS

| | | | |
|---|---|---|---|
| 4,149,403 A | 4/1979 | Muldary | 73/29.03 |
| 4,295,368 A | 10/1981 | Jannone | 374/54 |
| 4,509,679 A | 4/1985 | Longini | 236/94 |
| 4,542,993 A | 9/1985 | Mims | 374/42 |
| 4,547,078 A | 10/1985 | Long | 374/42 |
| 4,561,785 A | 12/1985 | Long | 374/42 |
| 4,645,635 A | 2/1987 | Yuen | 376/245 |
| 4,679,947 A | 7/1987 | Miller | 374/42 |
| 4,681,466 A | 7/1987 | Chien | 374/42 |
| 4,753,106 A | 6/1988 | Brenner | 73/29.01 |
| 4,768,593 A | 9/1988 | Novak | 166/295 |
| 4,832,503 A | 5/1989 | Dowling | 374/42 |
| 4,833,688 A | 5/1989 | Smith | 374/42 |
| 4,849,687 A | 7/1989 | Sims | 324/668 |
| 4,849,988 A | 7/1989 | Chien | 374/42 |
| 4,854,725 A | 8/1989 | Sims | 374/42 |
| 4,932,788 A | 6/1990 | Yeh | 374/35 |
| 5,031,465 A | 7/1991 | Redus | 73/861.04 |
| 5,031,466 A | 7/1991 | Redus | 73/861.04 |
| 5,035,146 A | 7/1991 | Chien | 73/861.04 |
| RE33,909 E | 5/1992 | Brenner | 73/29.03 |
| 5,327,772 A | 7/1994 | Fredricks | 73/25.04 |
| 5,363,905 A | 11/1994 | Rhiel | 165/279 |
| 5,421,209 A | 6/1995 | Redus | 73/861.04 |
| 5,422,276 A | 6/1995 | Colvin | 436/1 |
| 5,551,469 A | 9/1996 | Woerheide | 137/8 |
| 5,663,491 A | 9/1997 | Beer | 73/61.41 |
| 5,731,517 A | 3/1998 | Ma | 73/152.01 |
| 6,044,804 A | 4/2000 | Franke | 122/448.1 |
| 6,823,743 B2 | 11/2004 | Sato | 73/861.61 |
| 6,857,324 B2 | 2/2005 | Sato | 73/861.61 |
| 7,013,740 B2 | 3/2006 | Dutton | 73/861.354 |
| 7,021,126 B1 | 4/2006 | Badami | 73/112.03 |
| 7,056,038 B2 | 6/2006 | Silverbrook | 400/62 |
| 7,058,549 B2 | 6/2006 | Gysling | 702/189 |
| 7,069,976 B2 | 7/2006 | Lindgren | 165/11.1 |
| 7,121,152 B2 | 10/2006 | Winston | 73/861.42 |
| 7,125,473 B2 | 10/2006 | Anderson | 162/263 |
| 7,127,360 B2 | 10/2006 | Gysling | 702/45 |
| 7,152,003 B2 | 12/2006 | Loose | 702/45 |
| 7,171,315 B2 | 1/2007 | Loose | 702/45 |
| 7,220,365 B2 | 5/2007 | Qu | 252/70 |

METHOD AND SYSTEM FOR MEASURING TEMPERATURE AND PRESSURE IN DIFFERENT REGIONS TO DETERMINE STEAM QUALITY

FIELD OF THE INVENTION

The present invention relates generally to steam control systems, and more particularly to a method and system for monitoring the quality and/or purity of steam used in a decontamination system such as a steam sterilizer or a steam injection device for pharmaceutical or food processing.

BACKGROUND OF THE INVENTION

Steam has been used in decontamination systems, such as sterilizers or autoclaves located in hospitals, manufacturing settings, and laboratories to sterilize devices such as medical and dental instruments, laboratory instruments, production equipment, manufactured products, and other articles. Steam is also used for vulcanizing, cooking, melting, humidifying, and drying in process industries such as pharmaceuticals, foods, paper, automotive, and printing, etc.

Steam purity and steam quality are important properties of steam that will affect the efficacy of a decontamination process, such as steam sterilization. Steam purity is an expression of the quantity of non-water components (vaporous contamination) carried in the steam. Steam quality refers to the quantity of moisture present in the steam. If there is no moisture (i.e., no liquid water), then the steam is of 100% quality. Accordingly, "pure" steam has a liquid water content of 0%. It should be appreciated that steam quality relates to steam purity because liquid droplets in steam may contain dissolved solids that may be transmitted to the process.

In many healthcare and pharmaceutical applications, the minimum acceptable steam quality for a steam sterilizer or autoclave is 95%. If steam quality is below 95%, then "wet packs" (i.e., moisture droplets) may develop on articles after completion of a sterilization cycle. Consequently, reprocessing will be required, and/or batches of product may have to be discarded.

Aside from decontamination, many processes require steam that is dry and contains no superheat. Printing presses use steam to control static electricity and to precisely control the drying and shrinkage of the paper. Poor steam quality can upset the control. Wet steam can even cause the paper to tear, ruining a press run. Dairy applications inject steam directly into milk during pasteurization. Wet steam can carry contaminants and add too much water during the injection process.

A steam generator used to vaporize water can introduce contaminants into the steam, thereby reducing steam purity. For example, where the steam generator is a boiler, boiler chemicals can be introduced into the steam during priming or foaming of the boiler. These contaminants may cause corrosion or staining of the product or decontamination device (e.g., steam sterilizer) or articles to be processed by exposure to the steam.

Attempts have been made to check the quality of steam in an effort to reduce some of the problems caused by steam with an inappropriate quality. U.S. Pat. No. 4,561,785 issued to Long claims to disclose a "method and apparatus for determining the quality of typical steam used in steam flooding for secondary recovery of petroleum" by continuously leaking a portion of high-pressure steam out of the system. Although leaking hot steam out of a system may be acceptable for oil well fields, there are many situations where such a hazard is not acceptable.

Other methods of analysis have been attempted such as in U.S. Pat. No. 4,547,078 issued to Long where steam quality is measured at a specific point in time by "obtaining a sample of the liquid component of steam and determining the quality of steam in a vessel or the like, such as steam flowing in a line used for steam injection in an oil well. The steam quality is determined by the known method of comparing the concentrations of dissolved solids in the liquid sample and the feedwater."

These steam quality measurements are time consuming, inaccurate, and can expose operators to potentially unsafe conditions including scalding heat and deafening noise. Moreover, other approaches to measuring steam quality do not provide advanced warnings of problems with quality of the steam used in a process.

SUMMARY OF THE INVENTION

A method and system for monitoring the quality steam used in a process is disclosed. A pressure and temperature sensor is exposed to the steam on either side of a pressure drop device such as an orifice or pressure reducing valve. Pressure and temperature sensors are exposed to the steam on either side of a pressure drop. The measurements are transmitted to a controller that continuously calculates the steam quality or superheat value and issues an alarm if the steam quality is beyond a predetermined tolerance.

The foregoing summary does not limit the invention, which is defined by the attached claims. Similarly, neither the Title nor the Abstract is to be taken as limiting in any way the scope of the disclosed invention.

BRIEF DESCRIPTION OF THE DRAWINGS

Each of the drawing figures now described shows an exemplary embodiment of the present invention.

DETAILED DESCRIPTION OF THE PREFERRED EMBODIMENTS

Figure 1:
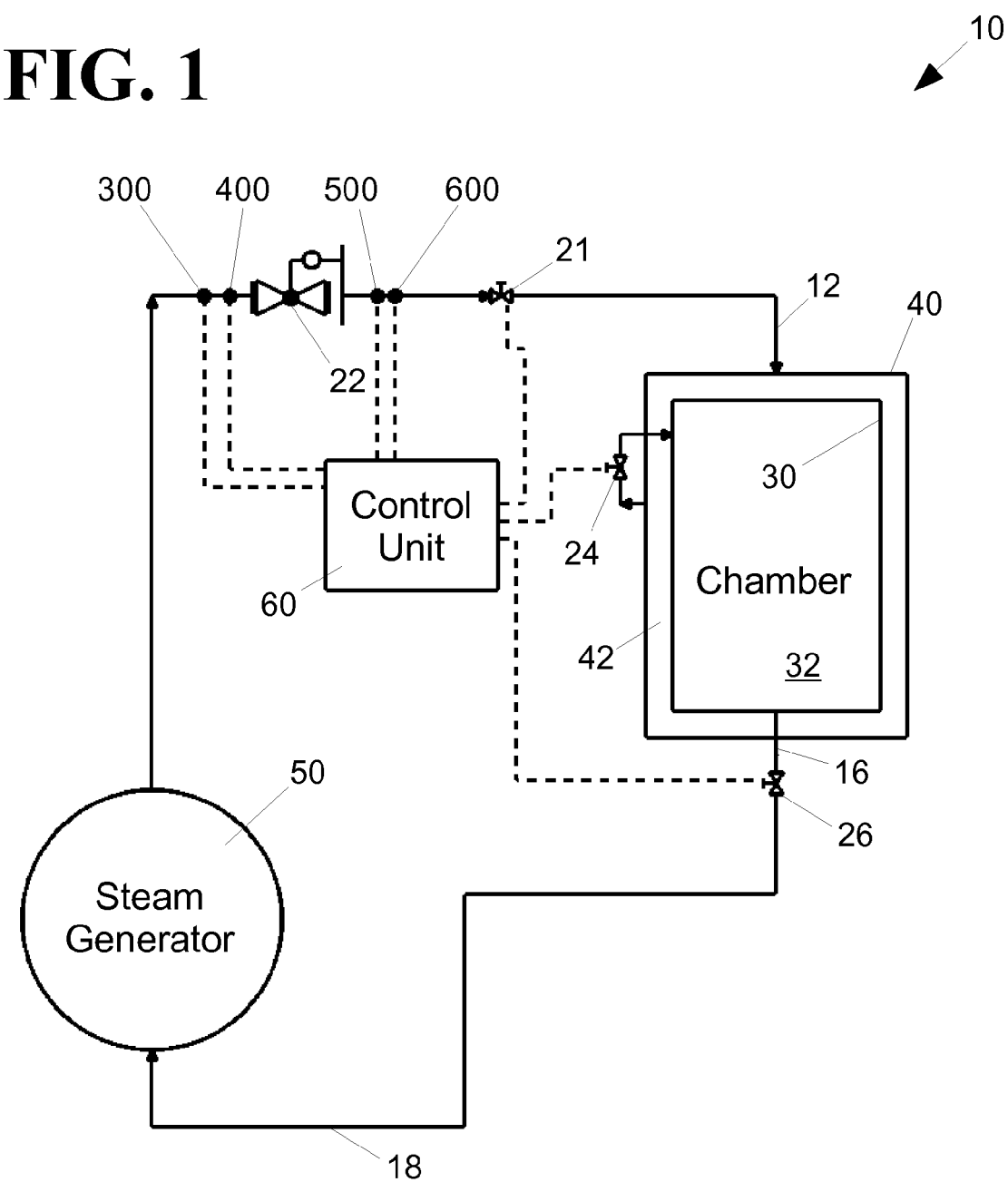
FIG. 1 is a side view of a steam pressure reducing station with inline steam testing of steam being delivered to a sterilization chamber.

Referring now to the drawings wherein the showings are for the purpose of illustrating the preferred embodiments. FIG. 1 shows a steam system 10 having a first temperature sensor 300, a first pressure sensor 400, a second temperature sensor 500, and a second pressure sensor 600 flanking an inline pressure reducing valve 22 for monitoring the purity and/or quality of steam used within the system. An "inline pressure reducer" is herein defined to be a mechanism structured to reduce the pressure of a gas to a pressure above atmospheric pressure, wherein the reduced pressure gas is provided to a device that performs a function other than gas analysis. In the illustrated embodiment, system 10 is a steam sterilization system for cleaning articles with steam. It should be understood that while a preferred embodiment of the present invention is described with reference to a steam sterilization system, it is contemplated that the present invention may be used in connection with other systems and facilities that utilize steam.

The steam sterilization system 10 generally comprises a vessel 30, an outer jacket 40, a steam generator 50, a control unit 60, and the first temperature sensor 300. The vessel 30 defines a chamber 32 that may be any shape, but is preferably cylindrical or rectangular. Articles to be sterilized are placed into chamber 32 for exposure to steam.

Steam is released from chamber 32 through an outlet conduit 16. A steam outlet valve 26 controls the release of steam from the chamber 32.

The outer jacket 40 surrounds vessel 30 and defines a steam region 42 between the vessel 30 and the outer jacket 40 for injection of steam. Like the vessel, the outer jacket 40 is preferably cylindrical or rectangular in shape. An input conduit 14 connects the steam region 42 with the chamber 32. A steam control valve 24 regulates the flow of steam between the steam region 42 and the chamber 32.

The steam generator 50 may produce steam through a variety of different heating methods. For example, the steam generator 50 may include a conventional natural gas boiler, an electrically powered resistive heating element, or the output of a high efficiency heat pump system. Water is supplied to a steam generator 50 through a water input conduit 18. Steam produced by the steam generator 50 is supplied to the steam region 42 by a first conduit 12. A sterilization valve 24 regulates the flow of steam into and out of the steam region 42. Steam may be intermittently provided to the sterilization unit in order to allow operators to add or remove surgical instruments from the sterilization unit without being scalded by steam. While the steam is flowing to the sterilization unit, and when the steam is stagnant, the temperature and pressure sensors may continuously provide updates on the quality of the steam. In one embodiment of the system, steam is provided to the sterilization unit for at least five minutes (and preferably 20 minutes) before the sterilization unit is isolated from the steam.

The control unit 60 is preferably a microprocessor or a microcontroller programmed on a computer readable medium to control operation of the system 10. In this regard, the control unit 60 sends control signals to operate valves 21, 22, 24 and 26.

Figure 2:
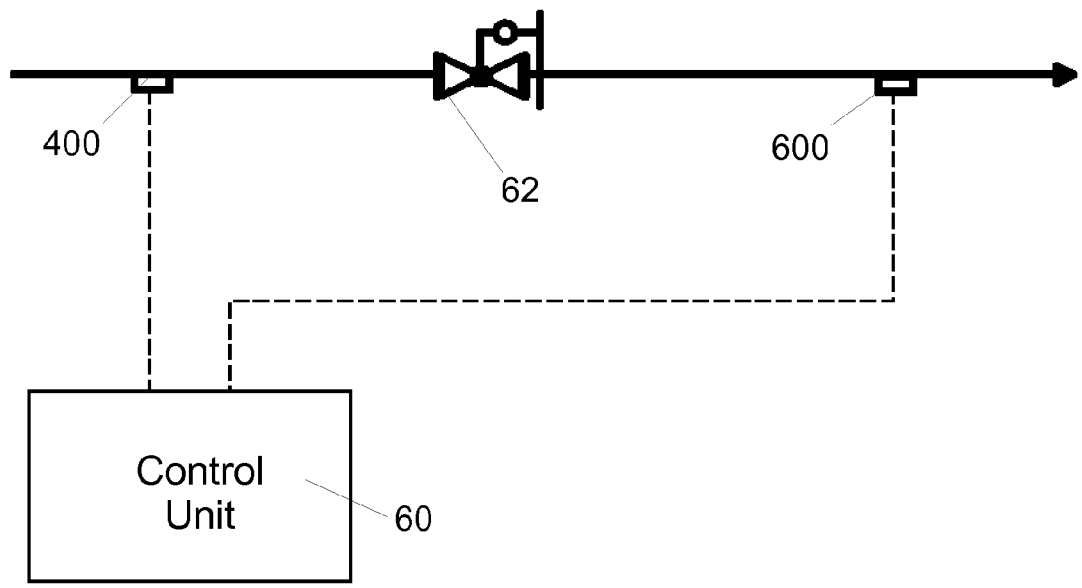
FIG. 2 is a schematic diagram of a sensor circuit for inline continuous monitoring of steam quality and superheat, the circuit having both pressure and temperature sensors upstream and downstream of a pressure reducing device.
Figure 3:
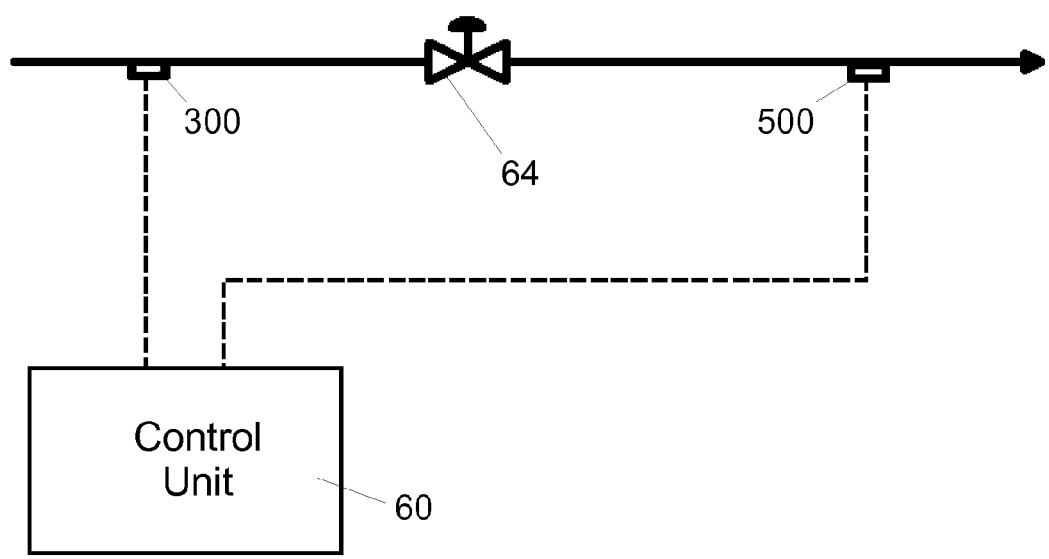
FIG. 3 is a schematic diagram of a sensor circuit for monitoring steam quality and superheat by sensing both the pressure and temperature upstream and downstream of a process control valve.
Figure 4:
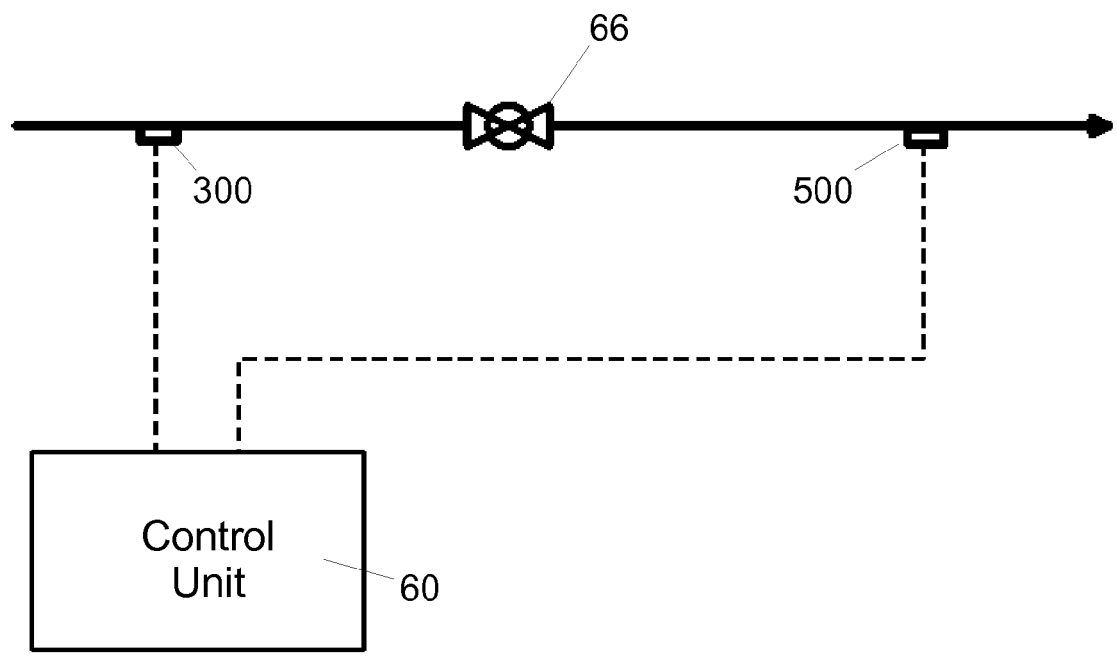
FIG. 4 is a schematic diagram of a sensor circuit for monitoring steam quality and superheat by sensing both the pressure and temperature upstream and downstream of an orifice plate.

The temperature sensors (300 & 500) and the pressure sensors (400 & 600) may take the form of any suitable sensing device responsive to changes in the pressure and temperature of steam used within the system 10. In FIG. 1, the temperature sensors are shown to be upstream of the pressure sensors, however temperature sensors may also be located downstream or parallel with the pressure sensors. Also, both pressure sensors may be between the temperature sensors and vice versa. Exemplary pressure sensors are shown flanking a pressure reducing reduction device 62 in FIG. 2 and exemplary temperature sensors are shown around a process control valve 64 in FIG. 3. In FIG. 4, sensors are located upstream and downstream of an orifice plate 66. In FIGS. 2 and 3, all of the steam mixture in the high pressure region passes through the inline pressure reducers.

The sensors 300, 400, 500, and 600 allow the control unit 60 to continuously compute and display (a) an indicator showing whether the steam is superheated or saturated; and (b) a second indicator showing the degree of superheat or the percentage of steam quality, also known as the dryness fraction.

The sensors 300, 400, 500, and 600 are preferably located near a dedicated pressure reducing valve 22, but it is also contemplated that they could be located in alternative locations with steam pressure differentials such as the steam control valve 24. Furthermore, it is contemplated that multiple control units could be included in system 10, to allow for monitoring of steam purity and/or steam quality at several locations therein. Alternatively, one control unit could calculate steam quality at a plurality of different locations having a plurality of different steam pressures and temperatures.

Physical properties of steam are stored on a computer readable medium in the control unit 60. Data tables or algorithms to compute steam quality and superheat are then used during the processing function to calculate steam quality and/or the degree of superheat. In this regard, it should be appreciated that the calculation required revolves around the measured pressure and temperature versus the known physical properties. Thus if 30 psia is measured by the pressure sensor downstream of the pressure reducing valve 22, but only 240° F. temperature is indicated by the temperature sensor downstream, then the steam quality is below 100%. The resulting quality percentage can be displayed, communicated as an alarm condition, or otherwise used for control of the process. The introduction of impurities (i.e., vaporous contaminants) into the steam will cause both the upstream and downstream conditions of the steam to change. For example, the introduction of air or carbon dioxide will result in changes to the steam temperature, but not the steam pressure. The presence of condensed water in the steam will generally cause a decrease in upstream temperature but not always, since the water can be at the saturation temperature. The presence of liquid water upstream will cause a drop in the temperature downstream. Accordingly, the control unit 60 can be used to ascertain a measure of steam purity and/or steam quality.

Figure 5:
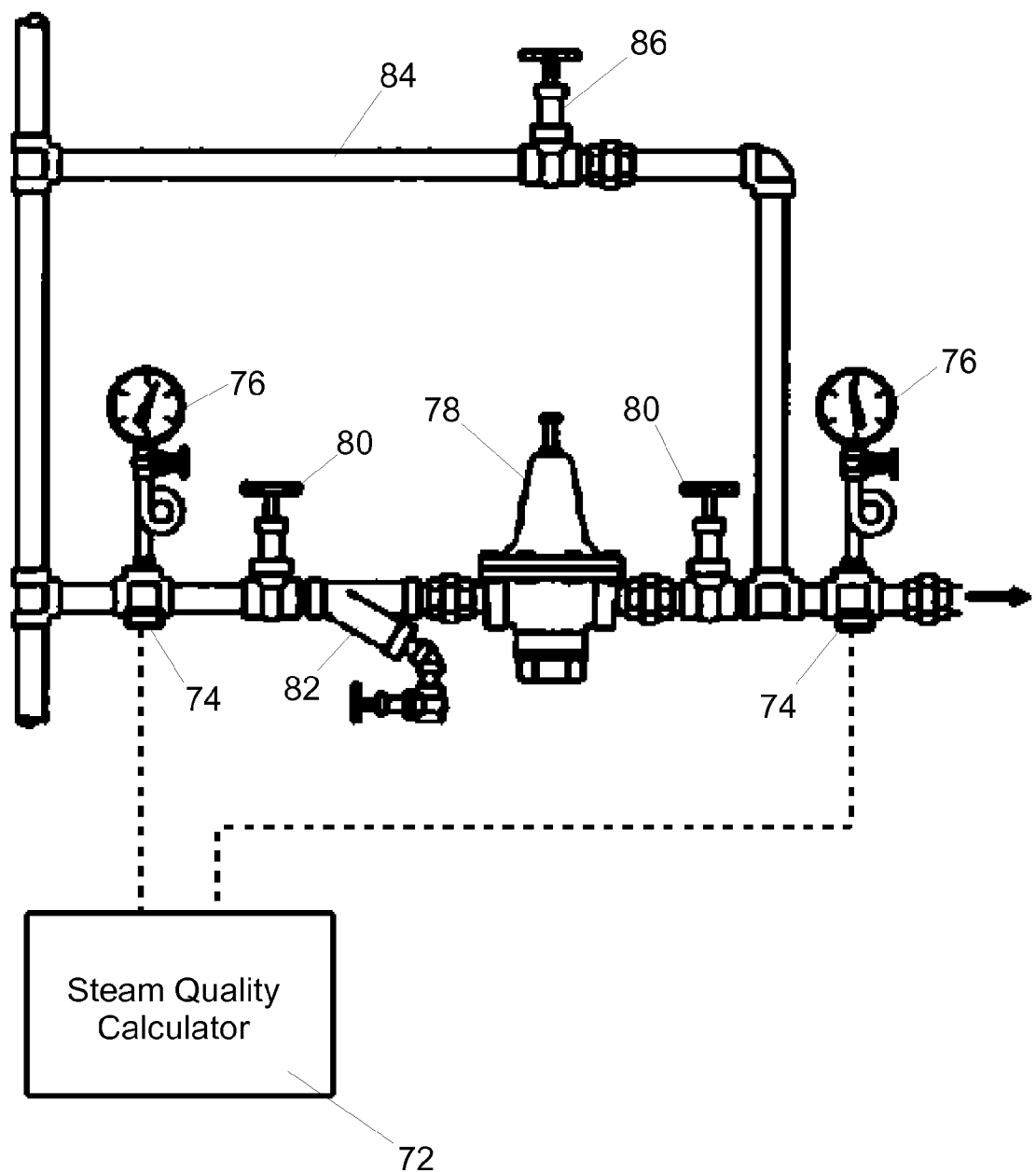
FIG. 5 shows a steam quality calculator continuously monitoring the quality of steam passing through a pressure reducing station

FIG. 5 illustrates an example of a steam quality calculator 72 continuously monitoring the quality of steam passing through a pressure reducing station. Thermocouples 74 and diaphragm gauges 76 for measuring pressure are located upstream and downstream of an inline steam pressure reducer 78. Isolation valves 80 are located upstream and downstream of both the pressure reducer and the pressure and temperature gauges. In the event that the steam quality drops below an acceptable threshold, the isolation valves may be utilized to stop the flow of steam through the pressure reducing station. A strainer 82 is located proximal to the pressure reducer 78 for removing steam condensate from the line. A bypass line 84 may be connected before and after the isolation valves to allow high pressure steam to be delivered downstream of the pressure reducer if desired. In the bypass line an isolation valve 86 selectively allows steam to flow through the isolation line.

Figure 6:
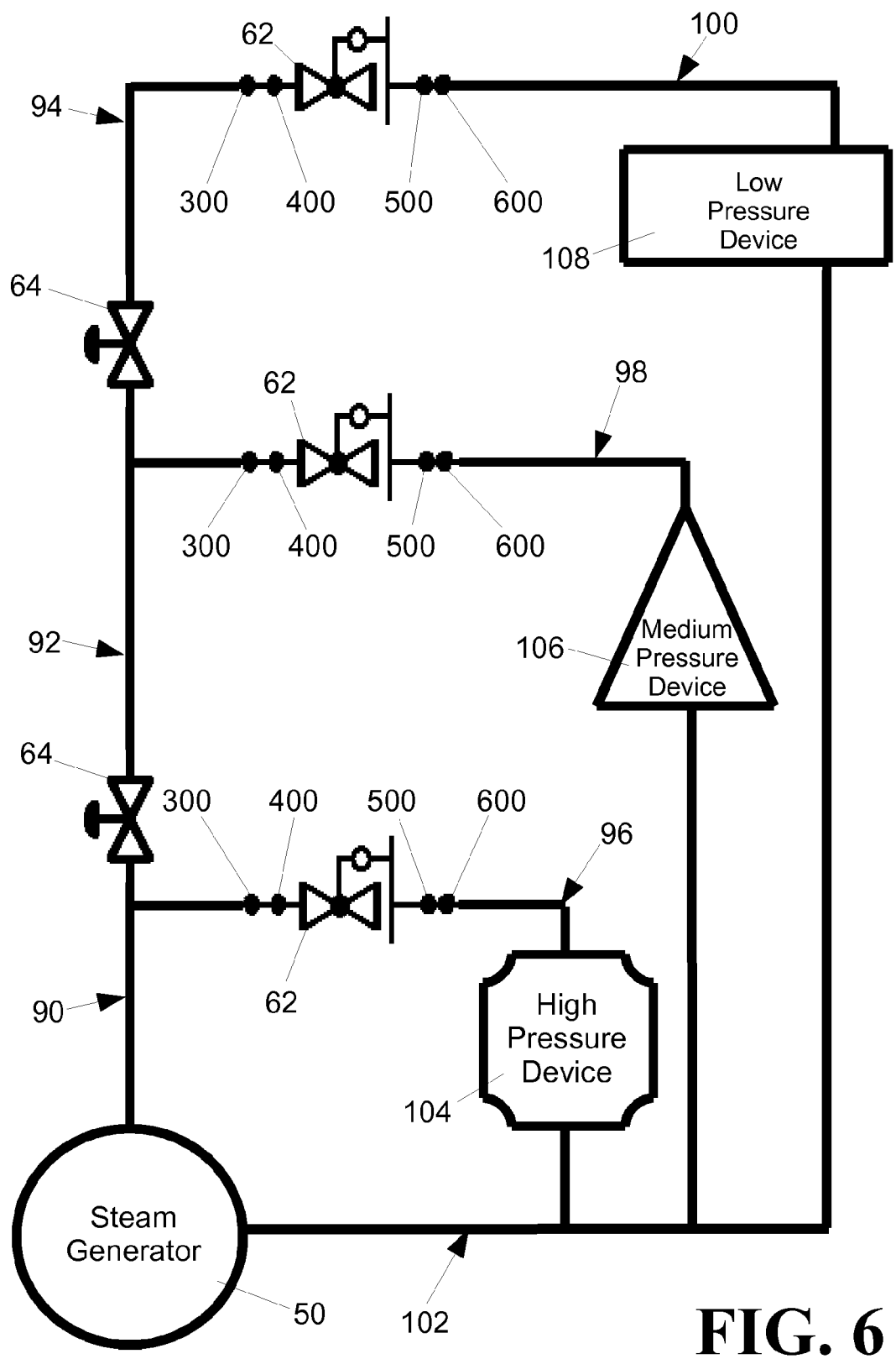
FIG. 6 is a schematic diagram of a steam system testing the steam quality of high, medium, and low pressure steam.

FIG. 6 illustrates an example of a steam system delivering high pressure, medium pressure, and low pressure steam to three different devices requiring three separate pressures of steam. A steam generator 50 provides high pressure steam (80-100 psi) to a high pressure steam artery 90. In passing through a inline process control valve 64 the pressure of the steam is reduced to a medium pressure (50-60 psi) in a medium pressure steam artery 92. A second inline process control valve 64 further reduces the pressure of the steam being provided to a low pressure steam artery 94, typically 10-15 psi. From the high pressure steam artery 90, a portion of the steam is diverted through a inline pressure reducer 62 to a first pressure line 96 connecting to a high pressure device 104 such as a washing or ironing machine. A portion of the steam from the medium pressure line is also diverted, and passes through a pressure reducer 62 to a second pressure line 98 connecting to a medium pressure device 106 such as a cleaning device for a kitchen. Finally, steam from the low pressure artery 94 passes through a third pressure reducer 62 to a third pressure line 100. Steam in the third pressure line is delivered to a low pressure steam device 108 such as a water heater, humidifier, or air handling unit coils. In addition to issuing warnings if the steam quality falls below a predetermined threshold, the steam system may control a desuperheating device to decrease the temperature of the steam if the temperature is above the steam saturation threshold for a given pressure. In an exemplary embodiment of the invention, all of the features shown in FIG. 6 may be enclosed with a single hospital building. In another embodiment, the steam has a pressure of 50-100 psig in the high region pressure region that drops to 25-35 psig in the low pressure region. In another exemplary system, the steam pressure drops from 60 psig in the high pressure region to 30 psig in the low pressure region.

A control unit (not shown) monitors and stores data signals from the plurality of pressure and temperature sensors (300, 400, 500, and 600) located upstream and downstream of the inline pressure reducers. Using the pressure and temperature data, the control unit is able to calculate the superheat and steam quality of the steam passing through the system. In the event that the steam quality provided to the devices falls below an acceptable range, the control unit 60 may close off the inline pressure reducers and isolate a selected number of devices. Alternatively, each pressure drop may have an independent analysis module with pressure sensors, temperature sensors, steam quality calculators, and alarms. The acceptable ranges of steam quality for the high-pressure device 104, the medium pressure device 106, and the low pressure device 108 may not be identical so the control unit 60 may only close off the inline pressure reducer to one of the devices. For example, the high pressure device may be a laundry unit with an acceptable steam quality ranging from 80% to 100% while the low pressure device 108 is a surgical instrument sterilizer with an acceptable steam quality range of 95% to 100%. In the event that the steam quality falls to 90%, the laundry unit would continue to operate normally while an alarm would sound for the sterilization unit. Alternatively, features at the pressure reducer directly upstream of the sterilization unit would act to close off the sterilization unit. In this example, the there is more than a 5% difference in the steam quality thresholds at which alarms sound for the laundry and surgical instrument sterilizer.

The steam analysis system may be an original part of the steam system, or the analysis system may be added after the steam system has been installed. When the analysis system is added to an already existing steam system, any existing pressure sensors, temperature sensors, pressure drops, data cables, and computer equipment may be utilized to reduce the cost of the steam analysis system.

The steam sterilization system 10 is operated by placing articles in the chamber 32 that is heated by pumping saturated steam from the steam generator 50 into the steam region 42, via the first conduit 12. After the steam region 42 is charged, saturated steam is injected into the chamber 32 via the input conduit 14. During a decontamination cycle, sensors 300-600 monitor the steam being provided to the chamber 32. In the event that it is determined that the steam does not comply with the required steam quality, then the control unit 60 may provide an audible and/or visual indicator to the operator. Furthermore, it may be necessary to take corrective action, including reprocessing the articles in the chamber. Data collected by the sensors 300-600 during decontamination cycles may be stored on a computer readable medium to provide historical data for verification of appropriate decontamination processing conditions.

At the end of a decontamination cycle, steam is pumped out of the chamber 32 via the outlet conduit 16, and the chamber 32 is evacuated to a pressure below atmospheric pressure to remove moisture from the chamber 32 or on articles therein. Steam leaving the chamber 32 may be condensed, and may drain down to be recycled at the steam generator 50 via the water inlet conduit 18 if the chamber is located at a higher position than the steam generator. If the steam generator is located above the chamber, the condensate may be pumped up to the steam generator.

The system controller may continuously calculate the steam quality at a plurality of different locations in the system by utilizing an array of pressure and temperature monitors. Utilizing data gathered from monitoring the system and stored data relating to the properties of steam mixtures, the system is able to calculate the steam quality. For example, if the measured upstream temperature is 143.32° C., the measured upstream pressure is 200 psi, the measured downstream temperature is 121.11° C., and the measured downstream pressure is 85.273 psi, then the steam quality may be determined by:

$$Q=200\times P_U+143.32\times T_U+85.273\times P_D+121.11\times T_D+K$$

wherein Q is the steam quality upstream, $P_U$ is the upstream pressure factor, $T_U$ is the upstream temperature factor, $P_D$ is the downstream temperature factor, $T_D$ is the downstream temperature factor, and K is a constant stored on the system controller.

While the principles of the invention have been shown and described in connection with specific embodiments, it is to be understood that such embodiments are by way of example and are not limiting. Consequently, variations and modifications commensurate with the above teachings, and with the skill and knowledge of the relevant art, are within the scope of the present invention. The embodiments described herein are intended to illustrate best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

I claim:

1. A method of calculating the quality of a steam mixture flowing from a high pressure steam source to a low pressure steam device, the steam mixture having an unknown quantity of liquid component, the method comprising the steps of:
    passing the steam mixture from a high pressure region to a low pressure region through a first inline pressure reducer;
    passing the steam mixture from the low pressure region to the low pressure steam device;
    measuring both the temperature and pressure of the steam in both the high pressure region and the low pressure region; and
    calculating the quality of the steam mixture from the measured temperatures and pressures.

2. The method of claim 1 wherein
all of the steam mixture from the high pressure steam source passes through the first inline pressure reducer.

3. The method of claim 1 wherein steam mixture in the high pressure region has a pressure of 50 to 100 psig, and the steam mixture in the low pressure region has a pressure of 25 to 35 psig.

4. The method of claim 1 further comprising
issuing an alarm if the calculated quality of the steam mixture is below 95%.

5. The method of claim 1 further comprising
passing the steam mixture from the high pressure region to a medium pressure region through a second inline pressure reducer;
passing the steam mixture from the medium pressure region to a medium pressure steam device;
triggering a first alarm for the low pressure device when the steam quality falls below a first threshold percentage;
triggering a second alarm for the medium pressure device when the steam quality falls below a second threshold percentage, wherein the first threshold percentage is more than 5% larger than the second threshold percentage.

6. The method of claim 5 wherein the low pressure device includes a surgical instrument sterilizer.

7. The method of claim 1 wherein
the temperatures and the pressures are continuously monitored, and
the steam quality is continuously calculated.

8. The method of claim 1 further comprising the step
draining a steam condensate down from the low pressure device to the high pressure steam generator; and
heating the steam condensate with the high pressure steam generator.

9. The method of claim 8 wherein
the low pressure device is intermittently operated and the low pressure device intermittently draws the steam mixture from the low pressure region;
while low pressure device is inoperative, the first inline pressure reducer blocks the flow of the steam mixture from the high pressure region to the low pressure region, the temperature and pressure of the steam in both the high pressure region and the low pressure region are continuously measured, and the quality of the steam mixture is continuously calculated.

10. A system for providing multiple pressures of a steam with a known steam quality to a plurality of steam utilizing devices, the system comprising:
a high pressure steam generator providing a high pressure steam to a high pressure artery,
a first inline pressure reducer transferring the steam from the high pressure artery to a medium pressure artery at a medium pressure;
a first inline pressure adapter connecting to the high pressure artery, the first inline pressure adapter withdrawing high pressure steam from the high pressure artery and provide steam at a first pressure to a first device;
a second inline pressure adapter connecting to the medium pressure artery, the second inline pressure adapter structured to withdraw medium pressure steam from the medium pressure artery and provide steam at a second pressure to a second device;
a first analysis module flanking the first pressure adapter to continuously monitor the steam quality of the steam provided to the first device,
a second analysis module flanking the second pressure adapter to continuously monitor the steam quality of the steam provided to the second device,
wherein each analysis module includes
an upstream inline temperature monitor and an upstream inline pressure monitor,
each monitor located upstream of the flanked adapter, and
a downstream inline temperature analyzer and a downstream inline pressure analyzer, each analyzer located downstream of the flanked adapter.

11. The system of claim 10 wherein
the first inline pressure adapter intermittently stops the flow of steam from the high pressure artery to the first device, and
the first analysis module monitors the steam quality of the steam while the flow of steam from the high pressure artery to the first device has been stopped.

12. The system of claim 10 wherein
the second analysis module issues an alarm when the monitored steam quality is below a higher threshold quality, and the first analysis module only issues an alarm when the monitored steam quality is below a lower threshold quality.

13. The system of claim 12 wherein the higher quality is 95%.

14. The system of claim 10 wherein
the high pressure steam generator,
the high pressure artery,
the first inline pressure reducer,
the medium pressure artery,
the first inline pressure adapter,
the first device,
the second inline pressure adapter,
the second device,
the first analysis module, and
the second analysis module
are all located within a single building.

15. The system of claim 14 further comprising a first drain line connecting to the first device and the high pressure steam generator, wherein a steam condensate drains down through the drain line from the first device to the high pressure steam generator.

16. The system of claim 10 wherein the second device is a surgical instrument sterilizer.

17. A system for monitoring the superheat and the steam quality of a steam delivered to a decontamination machine, the system comprising:
an inline pressure drop device for providing steam at a reduced pressure and defining a boundary between an upstream region and a downstream region;
an upstream pressure sensor for producing an upstream pressure signal corresponding to an upstream steam pressure exerted upon the upstream pressure sensor,
an upstream heat sensor for producing an upstream temperature signal corresponding to an upstream steam temperature,
a downstream pressure sensor for producing a downstream pressure signal corresponding to a downstream steam pressure exerted upon the upstream pressure sensor,
a downstream heat sensor for producing a downstream temperature signal corresponding to a downstream steam temperature,
a data storage device for receiving and recording
the upstream pressure signal, the upstream temperature signal,
the downstream pressure signal, and
the downstream temperature signal,
the data storage device including a table of fundamental water properties stored on a computer readable medium;
a processor for determining both the superheat and steam quality of the steam from the pressure signals, the temperature signals, and the table of fundamental water properties;
a warning device for displaying
a first indicator when the superheat of the steam is beyond a first threshold value, and
a second indicator when the steam quality of the steam is beyond a second threshold value.

18. A system according to claim 17, further comprising a steam generator, controlled by the processor controller, for providing steam to the inline pressure drop device.

19. A system according to claim 17, wherein the processor regulates a desuperheating process.

20. A system according to claim 17, wherein the system intermittently
provides steam to the decontamination device and
isolates the decontamination device from the steam.

21. The system of claim 20 wherein the system provides the decontamination device with steam for at least five minutes before the system isolates the decontamination device from the steam.

* * * * *